US010390797B2

(12) United States Patent
Shi et al.

(10) Patent No.: US 10,390,797 B2
(45) Date of Patent: Aug. 27, 2019

(54) SHEAR WAVE VELOCITY ESTIMATION USING CENTER OF MASS

(75) Inventors: Yan Shi, White Plains, NY (US); Hua Xie, Ossining, NY (US); Roy Peterson, Seattle, WA (US); Jean-Luc Robert, White Plains, NY (US); Vijay Shamdasani, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 518 days.

(21) Appl. No.: 13/995,522

(22) PCT Filed: Dec. 19, 2011

(86) PCT No.: PCT/IB2011/055768
§ 371 (c)(1),
(2), (4) Date: Aug. 14, 2013

(87) PCT Pub. No.: WO2012/085812
PCT Pub. Date: Jun. 28, 2012

(65) Prior Publication Data
US 2013/0317362 A1    Nov. 28, 2013

Related U.S. Application Data

(60) Provisional application No. 61/425,844, filed on Dec. 22, 2010.

(51) Int. Cl.
*A61B 5/00* (2006.01)
*A61B 8/00* (2006.01)
(Continued)

(52) U.S. Cl.
CPC .......... *A61B 8/5207* (2013.01); *A61B 5/0051* (2013.01); *A61B 5/7235* (2013.01);
(Continued)

(58) Field of Classification Search
None
See application file for complete search history.

(56) References Cited

U.S. PATENT DOCUMENTS

| 5,317,674 A * | 5/1994 | Muraji .............................. 706/9 |
| 2004/0068184 A1 | 4/2004 | Trahey |

(Continued)

FOREIGN PATENT DOCUMENTS

| EP | 0502701 A2 | 3/1992 |
| WO | 2011001333 A1 | 1/2011 |

(Continued)

OTHER PUBLICATIONS

Johnson, Francis S. "Physical cause of group velocity in normally dispersive, nondissipative media." American Journal of Physics 58.11 (1990): 1044-1056.*

(Continued)

*Primary Examiner* — Carolyn A Pehlke

(57) ABSTRACT

A device and a method for computing a weighted-average-based position of a shear wave in a temporal domain based on a sampling of shear wave displacements along a propagation path of the shear wave. The weighted-average-based position is, for example, by displacement observed at a plurality of times that correspond to sampling, and represents a time of arrival of the shear wave at a location being sampled along the propagation path. Further, times of arrival of the shear wave at respective locations along the propagation path are functionally related to known inter-location distances to derive shear-wave group velocity. The derived shear-wave group velocity serves as an input into algorithms for estimating a shear elasticity of a medium, such as a body tissue, for purposes of a clinical diagnosis and therapy assessment.

20 Claims, 5 Drawing Sheets

(51) Int. Cl.
 *A61B 8/08* (2006.01)
 *A61B 5/055* (2006.01)
(52) U.S. Cl.
 CPC ............ *A61B 8/4483* (2013.01); *A61B 8/485* (2013.01); *A61B 5/055* (2013.01); *A61B 5/4244* (2013.01); *A61B 2562/0204* (2013.01)

(56) References Cited

U.S. PATENT DOCUMENTS

| | | |
|---|---|---|
| 2007/0038095 A1 | 2/2007 | Greenleaf |
| 2008/0249408 A1 | 10/2008 | Palmeri |
| 2009/0069693 A1 | 3/2009 | Burcher |
| 2010/0016718 A1 | 1/2010 | Fan |

FOREIGN PATENT DOCUMENTS

| | | |
|---|---|---|
| WO | 2011007278 A2 | 1/2011 |
| WO | 2011064688 A1 | 6/2011 |

OTHER PUBLICATIONS

Hoskins, Peter R., Kevin Martin, and Abigail Thrush, eds. Diagnostic ultrasound: physics and equipment. Cambridge University Press, 2010.*
Kids Math, Equivalent Fractions (http://www.ducksters.com/kidsmath/fractions_equivalent.php, Nov. 13, 2012).*
Learn a Fact: 1x1 (http://www.multiplication.com/learn/multiply/1/x/1, Jan. 10, 2012).*
Dictionary entry for "material" (http://www.merriam-webster.com/dictionary/material).*
Ibach, H. et al. "Solid-State Physics" Motion of Electrons and Transport Phenomena, XP-002677804, 2009, p. 242.
Bronstein, I.N. et al "Taschenbuch der Mathematik", 1968, XP002677805, p. 342, fig. 317c.
Yamakoshi, Yoshiki et al "Ultrasonic Imaging of Internal Vibration of Soft Tissue under Forced Vibration", IEEE Transactions on Ultrasonics, Ferroelectrics, and Frequency Control, vol. 37, No. 2, Mar. 1990, pp. 45-53.
Urban, Matthew W. et al "Error Estimates in Shear Wave Speed and Tissue Material Properties in Shear Wave Dispersion Ultrasound Vibrometry", 2007 IEEE Ultrasonics Symposium. pp. 664-667.
Palmeri, Mark L. et al "On the Thermal Effects Associated with Radiation Force Imaging of Soft Tissue", IEEE Transactions on Ultrasonics, Ferroelectrics and Frequency Control, vol. 51, No. 5, May 2004, pp. 551-565.
Passmann, Christian "A 100 MHz Ultrasound Imaging System for Dermatologic and Ophthalmologic Diagnostics", IEEE Transactions on Ultrasonics, Ferroelectrics and Frequency Control, vol. 43, No. 4, Jul. 1996, pp. 545-552.
Nightingale et al "Shear Wave Velocity Estimation Using Acoustic Radiation Force Impulsive Excition in Liver In Vivo" 2006 IEEE Ultrasonics Symposium Proceedings.

* cited by examiner

SHEAR WAVE VELOCITY ESTIMATION USING CENTER OF MASS

FIELD OF THE INVENTION

The present invention is directed to detecting shear-wave time-of-arrival and, more particularly, to doing so based on shear-wave-induced displacement.

BACKGROUND OF THE INVENTION

Mechanical changes in living tissue correlate with pathological changes. As between healthy and pathological tissue, the shear elastic modulus (stiffness) and viscosity can vary significantly. With the advent of ultrasound elasticity imaging development over the past decade, many clinical studies have shown that tissue visco-elastic properties provide useful information to physicians for better cancer diagnosis and therapy assessment.

One method for measuring tissue mechanical properties is ultrasound shear wave elastography. It utilizes acoustic radiation force (ARF) to generate shear waves in soft tissue and subsequently tracks shear wave displacement to estimate tissue elasticity and viscosity. An application of this technique is the non-invasive measurement of liver stiffness to stage liver fibrosis and cirrhosis.

Interrogation by ultrasound, for purposes of medical imaging, often makes use of longitudinal waves. In body tissue, the ultrasound propagates in wave form. In effect, particles all along the propagation path vibrate, in place, back and forth, the vibration occurring in the direction of propagation. The vibrations create compressions and rarefactions. These are modeled as the peaks and valleys of a sinusoid. Energy is conveyed to the target and back by means of the oscillatory particle movements.

An ultrasound shear (or transverse) wave, by contrast, is characterized by back and forth in-place movement that is perpendicular to the direction of propagation. Oscillation one way creates the peaks, and the other way creates the valleys. The wave is comprised of components, each oscillating at its own frequency. It is the propagation speed of the wave envelope, or "group velocity", which is sought.

First, a focused longitudinal-wave push pulse is issued. It is a high intensity, long duration and narrow bandwidth signal. The push pulse creates a shear wave. The focal depth has been selected, at the outset, so that the shear wave travels through a region of interest (ROI). Push pulses can be fired repeatedly for multiple measurements to increase accuracy of the estimation of shear wave velocity. A typical repetition rate is 100 Hz.

A longitudinal-wave tracking pulse is issued to the ROI to assess, at the sampling point (or "lateral location"), the amplitude of the shear wave over a certain observation period (on the order of 10 ms). The measurement is of the body-tissue displacement perpendicular to the lateral direction of shear-wave propagation, that propagation being away from the region of excitation (ROE) at the push focus. The time period between the peak displacement and the push pulse responsible is called the time-to-peak (TTP). An example of the TTP technique is found in U.S. Patent Publication No. 2008/0249408 to Palmeri et al. (hereinafter "Palmeri"), the disclosure of which is incorporated herein by reference in its entirety.

The TTP is similarly determined for a number of lateral locations located, in mutual linear alignment along the propagation path, outward from the ROE. Time delays between peaks of different locations can be derived, as in acoustic radiation force impulse (ARFI) imaging.

Based on known distances between the lateral locations, a functional relationship can be estimated between distance the shear wave propagates and the time over which the distance is traversed.

From location to location, as the shear wave propagates outward from the ROE, geometrical spreading and viscosity cause the displacements to decay. Therefore, simply detecting, location by location, when a fixed displacement is achieved, is not a feasible means for determining group velocity.

In view of this, TTP assumes that a wave arrives at, or passes over, a lateral location when the peak displacement of the wave occurs at that location. It further assumes that the peak displacement outside the ROE travels at the group velocity of the shear wave.

Palmeri finds that these assumptions hold for purely elastic or mildly dispersive media.

SUMMARY OF THE INVENTION

What is proposed herein after is directed to addressing one or more of the concerns described above.

The present inventors have observed that wave-arrival time at a location can be characterized by the time at which the center of mass (COM) of the in-situ waveform exists at that location, and that the COM technique tends to yield shear-wave velocity values closer to ground truth than the TTP technique, especially for tissue with high shear modulus and/or shear viscosity. This is mostly applicable when lateral locations are close to the ROE, to yield the best signal-to-noise ratio (SNR). With the locations close to the ROE, dispersion will have more impact on TTP than on COM, thus making COM desirable. The inventors have further observed that COM is less prone to errors from multi-peaks when SNR is low.

As set forth in more detail below, a weighted average of sampling times is utilized to estimate the time corresponding to the COM of the waveform particular to the lateral location at which the sampling occurs in the body tissue under examination. The sampling can be performed at multiple lateral locations based on the same push. The push cycle may be repeated with different timings of the sampling to "fill out" each waveform.

Advantageously, the sampling-time factors of candidate summands, or the summands, of the weighted average can be selectively excluded if the displacement observed at the sampling time fails to exceed a threshold. Summands/factors that survive this first stage of filtering can also be required to exhibit a continuous displacement segment around peak and above a peak-neighborhood threshold. The segment can correspond to a curve fitted to the series of consecutive displacement values, and be deemed continuous if, for example, the sum of absolute distances of the values from the curve does not exceed a summed-deviation threshold.

Alternatively or in addition, lateral locations can likewise be selectively excluded based on sufficiently low displacement. The low displacement, in either case, can allow noise to assume a greater adverse impact. Accordingly, low signal-to-noise ratio (SNR) data is filtered out of the wave-arrival time computation, thereby increasing its accuracy.

In accordance with the present invention, a device is designed for using shear-wave-induced displacement measured at a location along a propagation path to compute a weighted average representative of arrival time of a shear wave at the location.

The device, in one aspect, is further configured for estimating shear-wave propagation speed based on a time the shear wave is present at a different location along the path.

In a sub-aspect, the speed is a magnitude of group velocity of the shear wave.

In another aspect, the weighting is based on the displacement.

In a particular aspect, the weighting is by the displacement.

In a further aspect, the values weighted correspond to times associated with sampling that detects the displacement.

In yet another aspect, the displacement is, based on whether it meets an instantaneous-displacement threshold, selectively excluded from computation of the average.

In one other aspect, the device is configured for the using, of the displacement, at a plurality of locations, the threshold varying with the location for which the respective average is being computed.

In a related sub-aspect, the threshold is based on peak displacement of material a medium comprises, the path being through the medium.

In a further specific sub-aspect, the threshold is directly proportional to the peak displacement.

In a yet further sub-aspect, the device is configured for the using at a plurality of locations to compute respective weighted averages representative of respective arrival times. The threshold is equal to the peak displacement multiplied by a factor invariant with location. The peak displacement varies with location In a still further sub-aspect, the factor dynamically varies based on a criterion.

In a particular, further sub-aspect, the criterion is based on a noise metric.

As an additional aspect, the device is configured for the using at a plurality of locations and for selectively excluding one or more of the plural locations.

In a particular sub-aspect, the device is further configured such that the selecting is dynamically based on a criterion.

In an associated sub-aspect, the criterion includes whether respective peak displacement exceeds a peak-displacement threshold.

In some embodiments, the device includes an ultrasound transducer configured for the measuring.

In some embodiments, the device is implemented as one or more integrated circuits.

In a different aspect, the weighted average is equal to the arrival time at the position.

In one further different aspect, the displacement is displacement of body tissue.

What is proposed herein is realizable as a device, method for making the device, computer program for carrying out the functionality of the device, signal for conveying the functionality and/or method for generating the signal. The method for generating comprises varying an electrical current applied to at least one of: a) a wire input to said device; and b) an antenna for transmitting, so as to, by the varying, generate the signal.

Details of the novel, shear-wave time-of-arrival technology are set forth further below, with the aid of the following drawings.

DETAILED DESCRIPTION OF EMBODIMENTS

Figure 1:
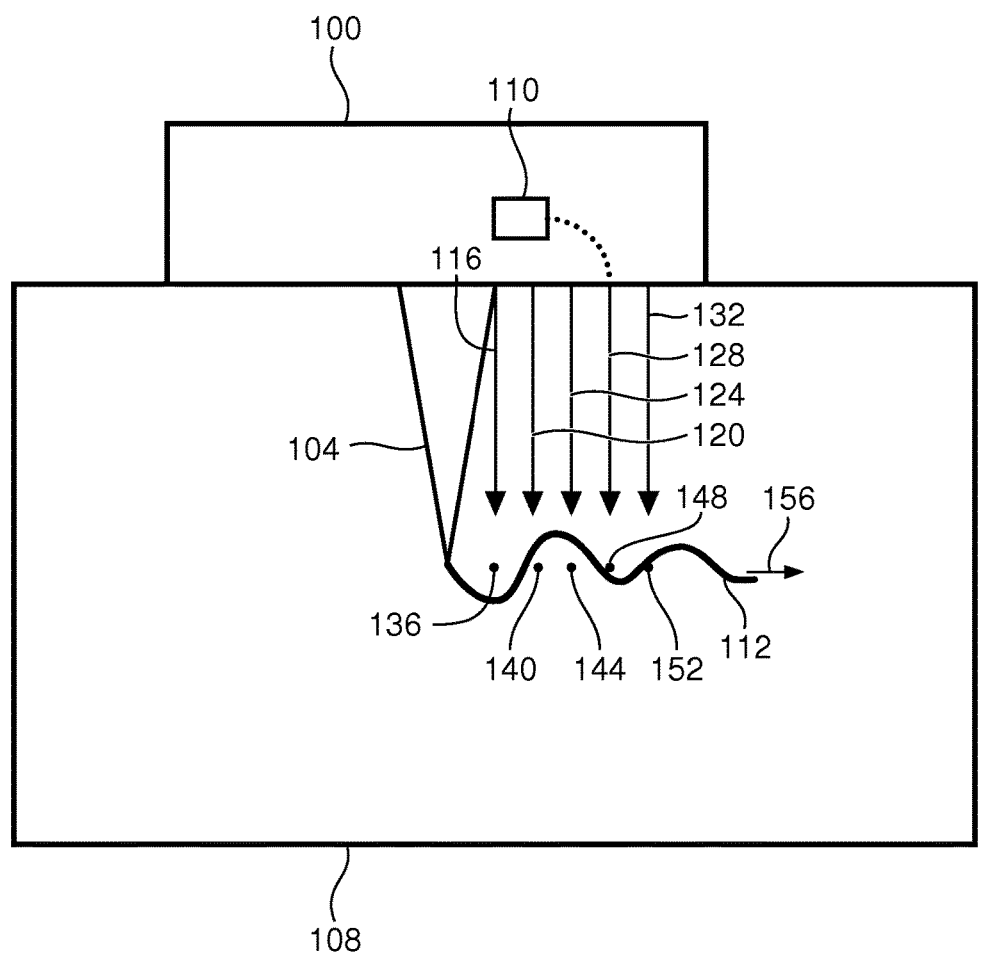
FIG. 1 is a schematic diagram exemplary of an ultrasound probe making measurements from a medium.

FIG. 1 is an example of an ultrasound probe 100 comprising an ultrasound transducer (not shown) firing a pushing beam 104 into a medium 108 such as body tissue. In particular, high intensity, narrow bandwidth signals are fired with a repetition rate of, for example, 100 Hz. The probe 100 includes an in-place, displacement-based weighter 110.

The resulting pushing beams 104 each cause a respective shear wave 112. Responsively, tracking beams 116, 120, 124, 128, 132 issue from the ultrasound probe 100, and their respective echoes (not shown) are received for processing.

The tracking beams 116-132 are utilized to measure shear-wave-induced vertical displacement in the body tissue 108 at different spatial locations 136, 140, 144, 148, 152 along a path 156 of the shear wave 112. Initially, reference pulses (not shown) are issued to each of the locations to provide a frame of reference for subsequent measurement of the displacement.

The shear wave 112 travels through soft body tissue at a speed that is roughly a thousand times slower than the 1540 meter (m) per second (s) at which an ultrasound wave propagates.

Responsive to the tracking beams 116-132 and to the previously-emitted reference pulses, respective echoes return to the probe 100. Using cross-correlation or phase-shift computations, displacement at the locations 136-152 is derived.

The displacement measured at a location 136-152 is, in accordance with what is proposed herein, utilized by the weighter 110 to determine when the shear wave 112 has arrived at the location, as explained in more detail further below. These determined times are usable to calculate a mechanical parameter of the tissue from which the displacement measurements were made. Examples of such mechanical parameters are shear elastic modulus, Young's modulus, dynamic shear viscosity, shear wave velocity and mechanical impedance.

For example, based on known distances between the locations 136-152 and known timings utilized in sampling, a functional relationship can be estimated between location-to-location distance the shear wave 112 propagates and the time period during which the inter-location propagation occurs. Linear regression can be used for making the determination. The slope of the regression line is indicative of the magnitude of the group velocity of the shear wave 112. The magnitude is the shear-wave propagation speed commonly used to calculate the shear elastic modulus of the tissue 108. A clinical determination regarding the tissue 108 can then be made.

Although five locations are shown in FIG. 1, more or fewer may be monitored.

The probe 100, or an apparatus that includes the probe, is implementable as the device of claim 1 for, by way of example, judging disease status or lesion malignancy.

Or, within or in communicative connection with the probe 100, control circuitry (not shown) serving as the device of claim 1 can take the form of one or more integrated circuits (ICs). One or more ICs in accordance with claim 1 can, alternatively, be configured for installation into existing ultrasound machines to enhance the aforementioned judging capability.

Shear waves are described herein above as being created by ARF which is non-invasive, but can alternatively be generated by coupling an external mechanical source to the site of interest. Imaging of the displacement can be performed using magnetic resonance imaging (MRI) instead of ultrasound, but MRI is relatively expensive and takes longer.

Figure 2:
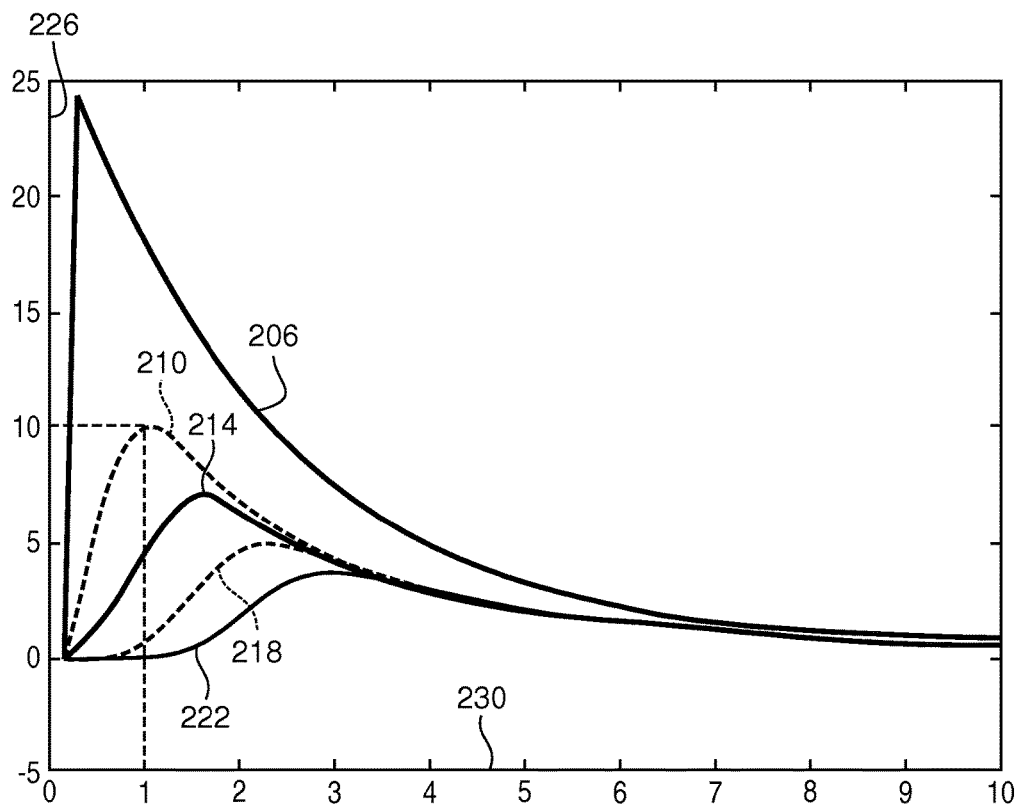
FIG. 2 is an exemplary series of location-based graphs of displacement over time, and shows formulas used in shear-wave velocity determination.

FIG. 2 shows, by way of illustrative and non-limitative example, five displacement-versus-time graphs, or "displacement curves", 206, 210, 214, 218, 222. They correspond to the five locations 136-152, respectively. The locations 136-152 are near the probe pushing focus, i.e., at the end of the pushing beam 104. They are disposed along the propagation path 156 in a line perpendicular to the axis of the probe 100, and they are located at the same depth as the probe pushing focus. Displacement 226 is in micrometers (μm) and time 230 is in milliseconds (ms). The spacing between successive locations 136-152 is 0.5 mm.

The weighter 110, which is illustratively shown operatively connected with the fourth tracking beam 128 but which likewise is connected to all the tracking beams 116-132, obtains the COM for each location 136-152 by taking a weighted average of the respective curve 206-222. The weighting is by displacement. The values being weighted correspond to times associated with sampling that detects the displacement. Thus, for the second location 140 and as shown in FIG. 2 by the broken line, a time value 230 of 1 ms would be weighted by the displacement 226 of 10 μm. Analogously, all, or some subset, of the values 230 could individually be weighted according to displacement 226, and added to form a sum 238. In the formula shown, "disp" stands for displacement 226. The variable "t" stands for the time 230 at which displacement is sampled. "Peak" stands for peak displacement 239 and "H" stands for instantaneous-displacement threshold factor 240, as discussed further below. The sum 238 is divided by a sum 242 of the displacements 226 used in the weighting, thereby forming a weighted average 244 represented by the symbol $t_{COM}$. The parameter, $t_{COM}$, is, for the given location 136-152, the COM position in the temporal domain, and is equal to the weighted average 244 computed. The parameter $t_{COM}$ represents the time of arrival of a shear wave 112 at the location 136-152, each location having its respective $t_{COM}$.

A propagation speed 246 is obtainable by the above-mentioned regression technique based on known distances 250 between locations 136-152 and the time period 254 between respective shear-wave time-of-arrivals 244, i.e., respective parameters $t_{COM}$. This is shown in FIG. 2, where Δd stands for the distance between two locations 136-152, and $\Delta t_{COM}$ stands for the difference between the two respective weighted averages 244 represented by the symbol $t_{COM}$.

Although the displacement curves 206-222 are shown as strictly positive-valued, the curve for any given location 136-152 may alternatively be strictly negative-valued, as discussed further below. Locations 136-152 for which the displacement curve 206-222 is a crest are comparable to each other for the purpose of calculating the propagation speed 246; likewise, locations for which the displacement curve is a valley are comparable for same purpose.

Advantageously, noise may be filtered from the displacement data, thereby making the weighted average 244 more robust.

There are a number of potential sources of noise. Some locations 136-152 may involve more noise. The first two locations 136, 140, for example, may be disposed within the push beam 104 so that pure shear wave propagation is no longer a valid assumption between these two locations. This depends on many factors, such as transducer frequency, f number, focal depth and tracking spacing.

Also, to penetrate to a deeper region of interest (ROI), a lower frequency of ultrasound is needed. The consequent longer wavelength sacrifices anatomical detail, thereby decreasing signal-to-noise ratio (SNR).

Patient respiration and heartbeat involve movement that can decrease SNR. If a tumor is being imaged, for instance, it may be closer or further from the heart or a major artery, resulting in more or less noise. The sampling can be time-gated to avoid these motion artifacts.

The noise can vary with the quality or type of ultrasound equipment used. For example, a scanner of reduced size or reduced transducer element size may produce more noise.

The noise has a greater adverse impact on smaller displacement-data used in the computation of arrival time 244.

Operationally, the locations 136-152 that are to be used in the computation of arrival time 244 are selected. For example, the first location 136 may selectively be excluded, as discussed herein above, for not reliably exhibiting pure shear-wave propagation. The exclusion, if any, by location can be pre-fixed, where, for example, the first location 136 is excluded. Exclusion can, alternatively or in addition, be dynamically determined based on certain criteria, such as peak, i.e., maximum, displacement having to be greater than a pre-set peak-displacement threshold.

Additionally, an instantaneous-displacement threshold varies by displacement curve 206-222 as the cutoff above which data can be trusted. The threshold can be based on peak displacement 239. It, for example, may be set equal to peak displacement multiplied by the instantaneous-displacement threshold factor 240 that is invariant with location. The factor 240 may be pre-fixed, e.g., at 50%. Or, it can be dynamically selected based on certain criteria. The criteria can entail a noise metric, such as SNR.

Figure 3:
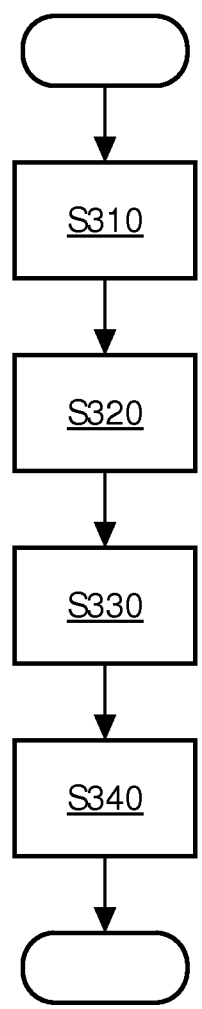
FIG. 3 is a flow chart illustrative of system operation.

As seen in FIG. 3, location exclusion may be pre-set by the operator, specifying which locations will be processed or excluded (step S310). Likewise, the operator can, if it is variable, enter the peak-displacement threshold, and can do the same for the instantaneous-displacement threshold factor 240 (step S320). After the sampling has been performed and subject to application of the inputs from the above steps S310, S320, dynamic location-exclusion is made according to the criteria set (step S330). In addition, displacement 226 that does not meet the instantaneous-displacement threshold is filtered out, i.e., not used in the computation of arrival time 244 (step S340).

Many different sampling schemes are possible.

At a pushing frequency of 100 Hz, typical for ARF-based shear-wave velocity measurement, a single wavelength passes by a given location 136-152 in 10 ms. With a tracking frequency, i.e., tracking pulse repetition rate (PRF), of 10 KHz, 100 samples could be taken if not for the time expended for the push 104. Thus, slightly fewer than 100 samples, e.g., 95 samples, can be taken during the 10 ms.

The locations 136-152 can be successively sampled in a concurrent manner. Thus, the first sample is at the first location 136, the second sample is at the second location 140, and so on. One pass consisting of five samples, one sample per each location 136-152, can be repeated 19 times, for example, for a single preceding push 104. Thus, each weighted average 244 can be based on 19 weighted values.

Provided the pushes 104 are uniform, the 19 values per location 136-152 can be supplemented with time-wise intermediate samples by observing displacement 226 over a number of pushes. With each subsequent push, the order of sampling is changed. Following the second push 104, for example, the first sample may be at second location, the second sample may be at the third location, and so on, with the fifth sample being at the first location. Following the third push, the sampling is shifted location-wise by one more location, and so on. By the time the shear-wave reaction to five consecutive pushes 104 has been measured, each of the locations 136-152 has been sampled at 95 equally-spaced time intervals that span the lifetime of the crest, or valley, or a portion thereof being sampled. With respective shear waves 112 of multiple pushes 104 being sampled, the weighted values of a single time-of-arrival computation 244 are based on sampling of temporally-different shear waves. Yet, they can be considered, for purposes of the computation, a single shear wave 112, due to uniformity of pushes 104. Thus, estimating shear-wave propagation speed is based on times the shear wave 112 is present at different locations 136-152, as gauged from data acquired from shear waves emanating from different pushes 104 that is used in the same calculation.

As another alternative for time-wise supplementation, the sampling order of the locations 136-152 can be kept constant, with the onset of sampling after each uniform push 104 delayed, further each time, by an inter-sampling time period. Thus, after the first push 104, the locations 136-152 are sampled in order, for 19 passes. After the second push 104, the same sampling order is retained, but the onset of sampling after the push is delayed. The delay, i.e., inter-sampling time period, is equal to the time between successive samples. As a consequence and by way of example, the first location 136 is sampled at a time-since-push that is slightly greater after the second push 104 than it was after the first push. After the third push, the sampling of the first location is further delayed, and so on, until the final, i.e., fifth, push. Again, as in the previous alternative, with five pushes 104 in total, each of the locations 136-152 has been sampled at equally-spaced time intervals that span the lifetime of the crest, or valley, or portion thereof being sampled. In the present alternative, in the pass immediately after the push 104, only the first location 136 is fully sampled; however, as evident from FIG. 2, the missing data would likely be filtered out anyway for not meeting the instantaneous-displacement threshold. The missing data could also be interpolated back, and then be subject to the filtering.

As another alternative, a multiline receive scheme, as mentioned in the Palmeri patent, collects more information per each tracking pulse. From each tracking or "transmission" pulse (or "transmit"), multiple receive lines are formed. Palmeri uses 4 in-parallel-directed receive lines, although more, such as 16 or 32 could be used. The receive lines are dynamically formed and spatially parallel.

To achieve a further increase in SNR, multiline-receive sample acquisition can be performed using retrospective dynamic transmit (RDT). RDT is described in the shear-wave sampling context in the commonly-assigned patent application, based on Philips Invention Disclosure 776394, entitled "Spatially-Fine Shear Wave Dispersion Ultrasound Vibrometry Sampling" to Burcher et al. (hereinafter "Burcher").

The Burcher patent application describes how a cycle of four spatially-staggered transmit and receive apertures can sample four spatial locations on a shear wave. As mentioned in Burcher, by extending the number of transmits in a cycle to five, eight spatial locations can be densely sampled at, for example, a spacing of merely 0.125 mm. Close inter-location spacing affords sampling closer to the push 104. This is beneficial in avoiding degradation of the measurements made of a shear-wave envelope whose magnitude perpendicular to the propagation axis decays over time.

Figure 4:
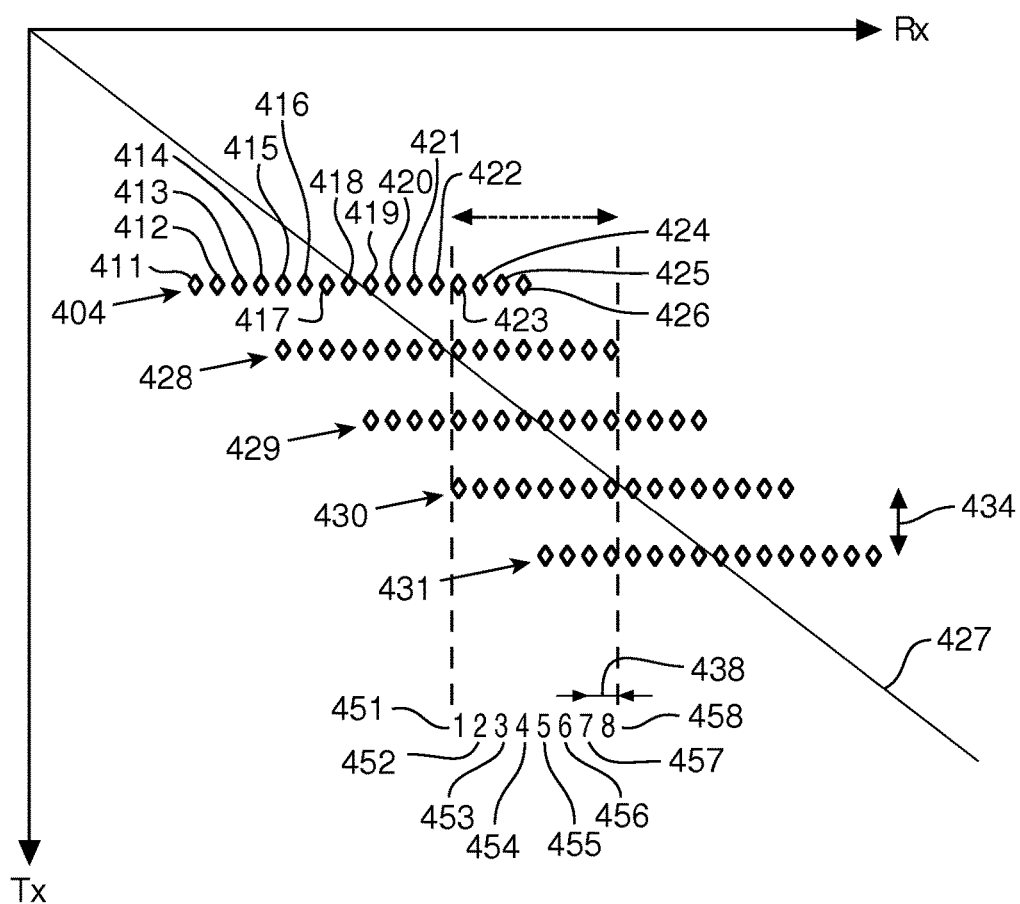
FIG. 4 is a schematic, transmit-receive diagram illustrating, by example, sample acquisition using retrospective dynamic transmit (RDT) as implemented on a 16× multiline beamformer.

FIG. 4 depicts an exemplary RDT scheme implemented on a 16× multiline beamformer, i.e., a beamformer that forms 16 receive lines from one transmit beam (or "transmit" for short).

With a multiline beamformer, sampling is by group of spatial locations. To each group, a transmission beam is issued. If the ROI is located at a different depth than the focus of the transmission beam, then the transmission beam will be broader than at the focus and will insonify the group of spatial locations. Alternatively, the beam can be weakly focused at the same depth as the ROI, with a breadth that is sufficient to insonify the group of spatial locations.

From the echoes of a transmission beam created from a single tracking pulse 404, 16× beamforming circuitry forms 16 in-parallel-directed receive lines 411-426 for making measurements of the shear wave 112. As indicated by a diagonal, sub-aperture tracking line 427, the first eight receive lines 411-418 are on one side of the center of the transmit, and the second eight receive lines 419-426 are on the other side.

Subsequent tracking pulses 428, 429, 430, 431 and the first tracking pulse 404 are all differently-timed. If the transmission A-line (or "tracking pulse") PRF is set equal to 10 kHz for example, the single tracking pulse 404 issues 100 μs before the next tracking pulse 428. 100 μs later, the next pulse 429 fires, and so on.

Each of the tracking pulses 404, 428, 429, 430, 431 is formed by a respective then-currently active sub-aperture of the tracking probe. The active sub-aperture is a subset of the transducer elements that are currently active to transmit ultrasound. Thus, for example, after the tracking pulse 404 fires, the currently active sub-aperture shifts (e.g., one or more elements on one side of the aperture are excluded and one or more elements on the other side are included). When the next tracking pulse 428 then fires, it occurs from the shifted sub-aperture. The spatial distance between adjacent apertures is referred to herein after as a transmit spacing 434, which, in the current example, is 0.5 mm. The focal point of the tracking pulse also shifts by the transmit spacing 434 between consecutive tracking pulses.

The 16 in-parallel-directed receive lines 411-426 (i.e., dynamically-formed receive lines that are spatially parallel) are formed from the echo data received after the transmit 404. Each of the receive lines 411-426 is formed by a receive sub-aperture. The receive sub-aperture is a subset of the transducer elements that contribute to a given receive line.

The spatial distance between the receive lines 411-426 is referred to hereinafter as a receive spacing 438. In this example, it is 0.125 mm, or one quarter of the 0.5 mm transmit spacing 434.

Making the receive spacing 438 a fraction of the transmit spacing 434 allows for more dense sampling, as will be discussed in more detail below.

All of the acquired echo radiofrequency data is saved in temporary storage. Retention of acquired data will continue as the sub-aperture shifts and eventually assumes its final position in the transducer array, i.e., so that an entire pass of data is acquired. In addition, data will be retained pass-to-pass.

Due to the shift in sub-aperture between the firing of the first tracking pulse 404 and the next tracking pulse 428, the last twelve receive lines 415-426 of that first pulse spatially overlap, respectively, with the first twelve receive lines of that next pulse. Likewise, due to the sub-aperture shift with each succeeding tracking pulse, the last twelve receive lines of the tracking pulse 428 overlap with the first twelve receive lines of the next tracking pulse 429, and so on.

By the time the fifth tracking pulse 431 fires, respective receive lines of all five tracking pulses 404, 428, 429, 430, 431 overlap and can be combined to form eight reconstructed A-lines corresponding to the eight locations 451-458.

The first reconstructed A-line for the location 451, for example, is formed from the first receive line 423, combined with the three respective receive lines of the immediately-subsequent tracking pulses 428-430, all four receive lines being aligned with the location. The combining occurs in accordance with retrospective dynamic transmit (RDT). The effect of RDT focusing can be analyzed using the virtual transducer approximation proposed by Passmann and Ermert in 1996. See C. Passmann & H. Ermert, "A 100-MHz ultrasound imaging system for dermatologic and ophthalmologic diagnostics," IEEE Trans. Ultrasonics, Ferroelectrics and Frequency Control, vol. 43, no. 4, pp. 545-52 (1996). This technique is further discussed in commonly-assigned U.S. Patent Publication Number 2009/0069693 to Burcher et al., entitled "Retrospective Dynamic Transmit Focusing for Spatial Compounding," (hereinafter "the '693 publication"). The disclosures of both publications are hereby incorporated herein by reference in their entirety.

The first reconstructed A-line for the location 451 is for measuring the shear wave 112 at a spatial location 451. Likewise, the immediately-subsequent reconstructed A-lines for the locations 452-458, which are laterally offset from the first reconstructed A-line for the location 451, are for measuring the shear wave 112 at the respective locations 452-458.

Although here four receive lines are combinable per reconstructed A-line, fewer receive lines can be combined. The number that are actually combined depends on the depth of the ROI and its consequent insonification coverage by tracking pulse. Also, the instant example is not limitative. Thus, the aperture shift may be to an extent that more or fewer receive lines are combinable to form a reconstructed A-line.

By virtue of the combining, depth of field (DOF), the region over which the transmit is well-focused, and signal-to-noise ratio (SNR) are increased. In comparing the reconstructed A-line for the location 451 to any of the receive A-lines from which it is reconstructed, the length over which its spatial resolution is useful has been increased by the greater DOF afforded by RDT.

A-line reconstruction based on potentially four receive lines begins with the first four reconstructed A-lines for the locations 451-454, and proceeds with each new tracking pulse. Thus, the next tracking pulse allows for the formation of four new reconstructed A-lines for the locations 455-458. Likewise, for the rest of the frame, each succeeding tracking pulse leads to the formation of a respective plurality of reconstructed A-lines, that plurality being, in the current example, made up of four reconstructed A-lines, in the event more locations are to be sampled.

With the scheme shown in FIG. 4, in which 8 locations 451-458 are sampled, 19 passes can be made following the push 104. In addition, data acquisition can entail multiple, e.g., 5, pushes. The locations can be sampled, as described above, with the onset of sampling after each push 104 delayed, to thereby enhance the weighted average calculations.

The shear wave 112 is therefore finely sampled, without a reduction in the pace by which tracking pulses issue.

When RDT combines transmits to interpolate intermediate transmit locations (as disclosed in the '693 publication), the sampling time (as well as the sampling location) is interpolated between transmits. In other words, in the case of pulse firing times, and in the case of the transmit locations upon firing (e.g., those along the sub-aperture tracking line 427 for transmits used in the reconstruction), they are interpolated by the same interpolation weightings used in RDT A-line reconstruction in the '693 publication.

Figure 5:
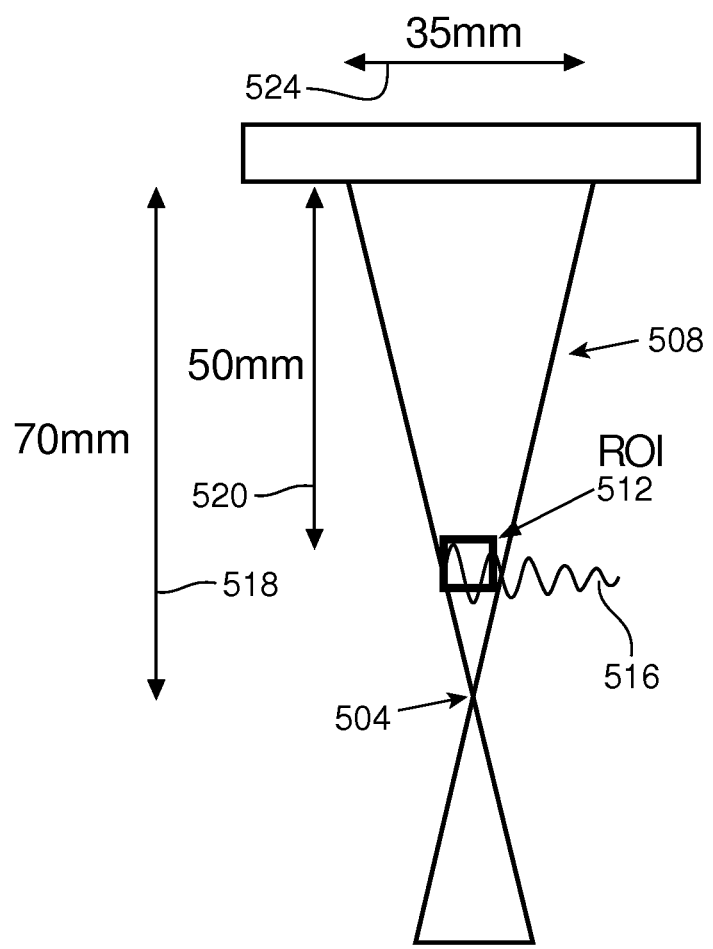
FIG. 5 is a schematic diagram demonstrating, in an RDT context, a possible placement of a detection beam transmit focus.

FIG. 5 demonstrates, in an RDT context, a possible placement of a focus 504 of a detection beam 508 formed by the tracking pulse 404. A region of interest (ROI) 512, as indicated by the square outline, is where a shear wave 516 is present. In order to ensure that insonification by the detection beam 508 spans the locations to be sampled by means of the receive lines to be acquired, it would be advantageous to place the focus 504 deep to the ROI 512. A physical focus position shown in FIG. 5 is at 70 mm, a common depth 518 for transmits insonifying a given point in the ROI and therefore to be RDT-combined. Although the detection beam 508 is wide at the depth 520 of the ROI 512, the RDT reconstructed detection beam will, at that depth, be narrow having the same width as at the (physical) focus 504. In effect and by way of example, from among the temporally-initial tracking pulse 404, and at least one laterally-offset tracking pulse 428-431 forming a transmit to be RDT-combined with that of the temporally-initial tracking pulse, at least some are focused to a common depth 518. A shallower transmit focus, to the depth 520, is reconstructed based on echo data from those of the pulses 404, 428-431 focused to the common depth 518.

This also allows the use of a larger transmit aperture 524, which may increase the total power that can be transmitted in the detection beam 508. More power affords greater sensitivity to the minute wave amplitude displacements 132, on the order of about 5 to 20 µm.

Alternatively, the focus 504 of the detection beam 508 may be placed shallow to the ROI 512.

RDT enjoys the above-noted advantages, despite its assumption that the tissue does not move between transmit events. If displacement does occur, then it will reduce the coherence between the combined transmits and lead to signal cancellation. This would therefore appear to be incompatible with the present technique, since the tissue is being displaced by the shear wave. However, in practice the displacements 226 are of such small magnitude (typically <20 µm) that this is a small fraction of the wavelength of the tracking pulse (e.g. 300 µm at 5 MHz). Therefore, the shear wave displacements 226 will not cause any significant loss in coherence during the transmit reconstruction.

To summarize, it is desirable to sample many locations to increase the number of measurements for robustness. The number of locations is limited by the maximum PRF as noted just above.

It is also of benefit that the lateral locations be close to the excitation point, i.e., the push focus, to avoid attenuation of the shear wave amplitude which makes it hard to measure the amplitude, although the first lateral location is limited in its closeness to the excitation point, due to near-field effects. Sufficiency of SNR may serve as a guide on how far away from the excitation point the lateral locations are to be placed in order to avoid the near-field artifacts. Closeness between adjacent locations is likewise desired to avoid attenuation, but is constrained by other engineering considerations.

By extracting more information from each tracking pulse fired, methodology and apparatus as proposed herein afford a more complete sampling of the shear wave displacement field. This therefore allows for more robust estimation of the shear wave speed and the elastic properties of the medium.

The weighted-average-based position in the temporal domain is computed based on the sampling of shear wave displacement along the propagation path. The weighting is, for example, by displacement observed at times corresponding to sampling and represents the time of arrival of the shear wave at the shear-wave propagation path location being sampled. In some embodiments, the computed shear-wave times of arrival at respective locations are functionally related to known inter-location distances to derive shear-wave group velocity. The derived velocity can serve as input into known algorithms for estimating shear elasticity of the medium, such as body tissue, for purposes of clinical diagnosis and therapy assessment.

Although methodology according to what is proposed herein can advantageously be applied in providing medical diagnosis for a human or animal subject, the intended scope of claim coverage is not so limited. More broadly, measuring a mechanical property of an elastic medium, in vivo, in vitro or ex vivo is envisioned.

While the invention has been illustrated and described in detail in the drawings and foregoing description, such illustration and description are to be considered illustrative or exemplary and not restrictive; the invention is not limited to the disclosed embodiments.

For example, all samples, e.g., 95, can be acquired for a single, particular location following its push, and then, following a next push, 95 for a next location, and so on. Here, the push-to-onset-of-sampling time would be the same for all locations. With uniformity of pushes, the sampling at different locations would correspond to the same, established waveform.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A signal embodying the above-described inventive functionality of the device 100, and for conveying it to the device, is formable by appropriately varying an electrical current. The signal can arrive by a device input wire, or be transmitted wirelessly by an antenna.

A single processor or other unit may fulfill the functions of several items recited in the claims. The mere fact that certain measures are recited in mutually different dependent claims does not indicate that a combination of these measures cannot be used to advantage.

What is claimed is:

1. A device comprising:
   an ultrasound transducer configured to fire pushing beams into a medium, the medium comprising a material, wherein each pushing beam of the pushing beams comprises a pushing beam focus and is configured to produce a respective shear wave along a propagation path through the medium, the ultrasound transducer further being configured to issue tracking beams;
   a multiline beamformer configured to form a plurality of spatially overlapping receive lines from respective echoes from the tracking beams, each respective tracking beam of the tracking beams comprising one transmit beam;
   a beamforming circuitry configured to measure shear-wave induced displacements in the medium at different spatial locations along the propagation path of the respective shear wave in response to the plurality of spatially overlapping receive lines; and
   a processor operatively connected with all the tracking beams,
   wherein the processor is configured to use the shear-wave-induced displacements, measured at the different spatial locations along the propagation path by the beamforming circuitry, to determine a time value of a center of mass of a waveform of the respective shear wave for each of the different spatial locations by computing a time-of-arrival weighted average of a displacement curve of the respective shear wave based on the plurality of spatially overlapping receive lines,
   wherein the time-of-arrival weighted average of the displacement curve is determined using time values of the displacement curve weighted by the respective shear-wave induced displacements of the displacement curve associated with the time values and measured by the beamforming circuitry at different sampling times associated with sampling that detects the shearwave induced displacements in the medium at each of the different spatial locations, and
   wherein the time value of the center of mass of the waveform of the respective shear wave for each of the different spatial locations, determined by computing the time-of-arrival weighted average of the displacement curve for each of the different spatial locations, is representative of an arrival time of the respective shear wave at a respective location of the different spatial locations, each respective location of the different spatial locations having a respective time-of-arrival weighted average.

2. The device of claim 1, wherein the ultrasound transducer is further configured to estimate a shear-wave propagation speed based on a time the respective shear wave is present at the different spatial locations along the propagation path.

3. The device of claim 2, wherein said shear-wave propagation speed comprises a magnitude of group velocity of said respective shear wave.

4. The device of claim 1, wherein said processor is further configured to selectively exclude from computation of the time-of-arrival weighted average, a particular displacement, based on whether the particular displacement meets an instantaneous-displacement threshold.

5. The device of claim 4, wherein the instantaneous-displacement threshold varies with the different spatial locations for which the respective time-of-arrival weighted averages are being computed.

6. The device of claim 1, wherein the different spatial locations comprise a plurality of different spatial locations, and wherein said processor is further configured to selectively exclude one or more of the plurality of locations from computation of the time-of-arrival weighted average.

7. The device of claim 6, wherein the selectively excluding of the one or more of the plurality of locations is dynamically based on a criterion.

8. The device of claim 7, wherein said criterion is based on whether a respective peak displacement exceeds a peak-displacement threshold.

9. The device of claim 1, wherein the device is implemented as one or more integrated circuits.

10. The device of claim 1, wherein said time-of-arrival weighted average is equal to the arrival time of the respective shear wave at a respective location of the different spatial locations.

11. The device of claim 1, wherein said shear-wave induced displacements comprise displacements of a body tissue.

12. The device of claim 2, wherein the time value of the center of mass of the waveform of the respective shear wave for each of the different spatial locations is determined such that a sum of shear-wave induced displacement values multiplied by corresponding time values of the shear-wave induced displacement values is divided by a sum of the shear-wave induced displacement values, wherein an individual shear-wave induced displacement value is greater than an instantaneous-displacement threshold, the instantaneous-displacement threshold determined by multiplying a peak displacement of the material, caused by a respective shear wave at a particular location of the different spatial locations, by an instantaneous-displacement threshold factor.

13. The device of claim 12, wherein the instantaneous-displacement threshold is directly proportional to said peak displacement.

14. The device of claim 13, wherein the processor uses a plurality of different spatial locations to compute the respective time-of-arrival weighted averages representative of respective arrival times, and wherein the instantaneous-displacement threshold is further equal to said peak displacement multiplied by a factor invariant with location, said peak displacement varying with location.

15. The device of claim 14, wherein said factor is dynamically varying based on a criterion.

16. The device of claim 15, wherein said criterion is based on a noise metric.

17. A method for detecting shear-wave arrival, said method comprising acts of:
configuring an ultrasound transducer to fire pushing beams into a medium, the medium comprising a material, wherein each pushing beam of the pushing beams comprises a pushing beam focus and is configured to produce a respective shear wave along a propagation path through the medium;
configuring the ultrasound transducer to issue tracking beams;
configuring a multiline beamformer to form a plurality of spatially overlapping receive lines from receive respective echoes from a respective tracking beam of the tracking beams, each respective tracking beam of the tracking beams comprising one transmit beam;
configuring a beamformer circuitry to measure shear-wave induced displacements in the medium at different spatial locations along the propagation path of the respective shear wave in response to the tracking beams and the respective received echoes plurality of spatially overlapping receive lines; and configuring a processor to use the shear-wave-induced displacements, measured at the different spatial locations along the propagation path by the beamforming circuitry, to determine a time value of a center of mass of a waveform of the respective shear wave for each of the different spatial locations by computing a time-of-arrival weighted average of a displacement curve of the respective shear wave based on the plurality of spatially overlapping receive lines,
wherein the time-of-arrival weighted average of the displacement curve is determined using time values of the displacement curve weighted by the respective shear-wave induced displacements of the displacement curve associated with the time values and measured by the beamforming circuitry at different sampling times associated with sampling that detects the shearwave induced displacements in the medium at each of the different spatial locations, and
wherein the time value of the center of mass of the waveform of the respective shear wave for each of the different spatial locations, determined by computing the time-of-arrival weighted average of the displacement curve for each of the different spatial locations, is representative of an arrival time of the respective shear wave at a respective location of the different spatial locations, each respective location of the different spatial locations having a respective time-of-arrival weighted average.

18. The method of claim 17, wherein the time value of the center of mass of the waveform of the respective shear wave for each of the different spatial locations is determined such that a sum of shear-wave induced displacement values multiplied by corresponding time values of the shear-wave induced displacement values is divided by a sum of the shear-wave induced displacement values, wherein an individual shear-wave induced displacement value is greater than an instantaneous-displacement threshold, the instantaneous-displacement threshold determined by multiplying a peak displacement of the material, caused by a respective shear wave at a particular location of the different spatial locations, by an instantaneous-displacement threshold factor.

19. A non-transitory computer readable medium comprising computer instructions which, when executed by a processor, configure the processor to perform the acts of:
configuring an ultrasound transducer to fire pushing beams into a medium, the medium comprising a material, wherein each pushing beam of the pushing beams comprises a pushing beam focus and is configured to produce a respective shear wave along a propagation path through the medium;
configuring the ultrasound transducer to issue tracking beams;
configuring a multiline beamformer to form a plurality of spatially overlapping receive lines from respective echoes from the tracking beams, each respective tracking beam of the tracking beams comprising one transmit beam;
configuring a beamformer circuitry to measure shear-wave induced displacements in the medium at different spatial locations along the propagation path of the respective shear wave in response to the plurality of spatially overlapping receive lines; and using the shear-wave-induced displacements, measured at the different spatial locations along the propagation path by the beamforming circuitry, to determine a time value of a center of mass of a waveform of the respective shear wave for each of the different spatial locations by computing a time-of-arrival weighted average of a displacement curve of the respective shear wave based on the plurality of spatially overlapping receive lines, wherein the time-of-arrival weighted average of the displacement curve is determined using time values of the displacement curve weighted by the respective shear-wave induced displacements of the displacement curve associated with the time values and measured by the beamforming circuitry at different sampling times associated with sampling that detects the shear-wave induced displacements in the medium at each of the different spatial locations, and wherein the time value of the center of mass of the waveform of the respective shear wave for each of the different spatial locations, determined by computing the time-of-arrival weighted average of the displacement curve for each of the different spatial locations, is representative of an arrival time of the respective shear wave at a respective location of the different spatial locations, each respective location of the different spatial locations having a respective weighted time-of-arrival average.

20. The non-transitory computer readable medium of claim 19, wherein the time value of the center of mass of the waveform of the respective shear wave for each of the different spatial locations is determined such that a sum of shear-wave induced displacement values multiplied by corresponding time values of the shear-wave induced displacement values is divided by a sum of the shear-wave induced displacement values, wherein an individual shear-wave induced displacement value is greater than an instantaneous-displacement threshold, the instantaneous-displacement threshold determined by multiplying a peak displacement of the material, caused by a respective shear wave at a particular location of the different spatial locations, by an instantaneous-displacement threshold factor.

* * * * *